United States Patent [19]

Eisinger

[11] 4,299,819

[45] Nov. 10, 1981

[54] PROCESS FOR TREATING BURN VICTIMS

[75] Inventor: Magdalena G. Eisinger, Demarest, N.J.

[73] Assignee: Sloan-Kettering Institute for Cancer Research, New York, N.Y.

[21] Appl. No.: 75,375

[22] Filed: Sep. 13, 1979

Related U.S. Application Data

[62] Division of Ser. No. 749, Jan. 2, 1979.

[51] Int. Cl.³ .................... A61K 35/12; A01N 1/02
[52] U.S. Cl. ........................................ 424/95; 435/1; 435/241
[58] Field of Search ............... 424/95, 366; 435/1, 435/240, 241

[56] References Cited

U.S. PATENT DOCUMENTS 4,016,036  4/1977  Green et al. ................. 435/241

OTHER PUBLICATIONS

Kitano et al.–Biochem. of Cutaneous Epidermal Differentiation, Ed. by Seiji, (1977), pp. 319–335.
Rheinwald et al.–Cell, vol. 6, Nov. 1975, pp. 313–334.
Eagle–Science, vol. 174, Oct. 29, 1971, pp. 501–503.
Eagle–J. Cellular Physiology, vol. 82, No. 1, Aug. 1973, pp. 1–7.
Willmer–Cells & Tissue in Culture, vol. 1 (1965), pp. 24 & 25.

*Primary Examiner*—Sam Rosen
*Attorney, Agent, or Firm*—Sprung, Felfe, Horn, Lynch & Kramer

[57] ABSTRACT

Burn victims are treated with human epidermis cells grown in tissue culture by separating the epidermis in human skin from the dermis, dissociating the epidermis into epidermal cells, and growing the epidermal cells in a tissue culture medium having a pH of from about 5.6 to 5.8.

13 Claims, No Drawings

PROCESS FOR TREATING BURN VICTIMS

The invention described herein was made in the course of work under a grant or award from the Department of Health, Education and Welfare.

BACKGROUND

This invention relates to a process for growing human epidermis in vitro for, among other things, treating burn victims.

Human diploid epidermal cells have been grown in culture in the presence of fibroblasts. However, proliferation of fibroblasts must be controlled so that the epidermal cell population is not overgrown. This requires plating epidermal cells with irradiated 3T3 (mouse) cells. Rheinwald and Green, Cell, 6, 331-334, Nov. 1975. This technique requires the presence of dermal components and is not useful for treating humans.

Kitano et al in Biochemistry of Cutaneous Epidermal Differentiation, Ed. by Seiji et al, University Park Press, 1977, pp. 319-335, suggest that keratinocytes dispersed from epidermis grow without dermal components in a suitable culture medium (30% fetal bovine serum) and show some signs of differentiation. However, this technique is not reproducible.

SUMMARY

This invention provides a method for growing human epidermal cells in vitro in the absence of dermal components to produce single or multi-layered pure human epidermis which can be used directly for example in the treatment of burn victims.

The method of the invention includes the steps of (i) separating the epidermis in human skin from the dermis;

(ii) dissociating the epidermis into epidermal cells; and (iii) growing the epidermal cells in a tissue culture medium having a pH of from about 5.6 to about 5.8.

DESCRIPTION

The epidermis of human skin can be separated from the dermis using the Medawar trypsin technique. *Nature*, 148, 783-4 (1941).

The separated epidermis is dissociated into individual epidermal cells mechanically and the cells are then seeded into a suitable tissue culture medium at the required pH. It is preferred to remove any remaining clumps or pieces of tissue, for example, by filtration, prior to seeding. This removes non-viable cells that otherwise interfere with growth of the epidermal cells.

A suitable tissue culture medium has a pH in the range of about 5.6-5.8 and supports and promotes the growth of the epidermal cells. The growing is preferably carried out in a plastic tissue culture vessel but other cell growth techniques can also be used.

A preferred culture medium contains about 5-15% by volume, preferably about 10%, fetal calf serum which is commercially available from a number of sources. Hydrocortisone can be added to the medium to make the colony morphology more orderly and distinctive. Rheinwald and Green, *Cell*, 6, 331-44 (1975). It is also desirable to reduce the amount of fetal calf serum to about 5% once the cells become attached to the vessel.

Seeding of the epidermal cells in the culture medium is preferably in the range of about $5-8 \times 10^5$ cells/ml which has been found to promote optimal growth of the epidermis.

Growth in the medium is preferably carried out at a temperature of about 35°-36° C. under relative humidity of about 80% in the presence of 5% carbon dioxide and 95% atmospheric air.

To apply or transfer the single or multi-layered epidermal sheet grown in vitro according to the invention, a transfer member such as the dermal side of pig skin or a collagen sponge is used. The epidermal sheet becomes sufficiently adhered to the transfer member (after the edges of the sheet are cut from the tissue vessel with sharp scalpel) so that it can be removed from the tissue vessel and applied, for example, to an afflicted area on a burn victim. To facilitate host acceptance, the skin of the burn victim is used but this is not essential.

The invention is notable for the absence of any dermal components which have previously been thought to be essential for human epidermal cell growth in vitro. This system offers an opportunity to grow human epidermal cells which have retained the potential to differentiate into multilayered structures. These, in turn, can be used for transplantation mainly in cases of burn patients, where rapid enlargement of the epidermis is necessary to cover the affected area. Because of the absence of any dermal components, these cells can be also used for testing of the effects of different drugs and/or carcinogens on the human epidermis. Thus the invention finds use for treatment of burn patients either as autografts or homografts, for the testing of drugs and/or carcinogens, for the growth of other epidermal cells such as conjunctival epidermis of corneal cells and for the growth of viruses which require epidermal cells which differentiate, such as the human wart virus.

The addition of the epidermal growth factor, and/or of specific nutrients required by the epidermal cells can be used for continued in vitro survival.

The following example is intended to illustrate the invention without limiting same. Abbreviations used are as follows:

U PNC—units of penicillin

STM—streptomycin

ATV—(MADIN, S.H. and DARBY, N.B., Jr.: Established cell lines of normal and adult bovine and ovine origin. Proc. Soc. Exp. Biol. Med. 98:574-576 (1958).) NaCl, 8 gm/l; KCl, 0.4 gm; dextrose, 1 gm; NaHCO$_3$, 0.58 gm; trypsin (DifcO 1:250), 0.5 gm; versene (disodium salt), 0.2 gm; distilled water to 1000 ml.

EDTA—Ethylendiamine tetraacetic acid, disodium salt (Sigma).

MEM—Minimum Essential Medium (Eagle) with Earle's Salts.

GMEM—10% Fetal calf serum (FCS), 100 U PNC/ml, 100 g STM/ml, 0.6 mcg Fungizone/ml, 0.5 mcg hydrocortisone/ml, L-glutamine 200 mM 0.292 g/ml, and MEM - non-essential amino acids 10 mM (Grand Island Biol. Co.) 1 ml/100 ml.

Full thickness or split thickness human skin can be used. The skin can be obtained from any part of the body, including foreskin. If full thickness skin is used, the dermis should be trimmed down as far as possible. The skin is washed in MEM with 1,000 U PNC/ml, 1,000 mcg/ml STM and 3.00 mcg/ml Fungizone for 30 min.; followed by two washes for 10 min. each in the same medium. Two additional washes 10 min. each are in MEM with 10 times less antibiotics than above. The skin is then cut into 4 mm$^2$ pieces and immersed into a 0.02% EDTA (prepared in distilled H$_2$O) for 10–15 min. Afterwards, the pieces are transferred to a 0.25% trypsin (Trypsin 1:250 "Difco" certified) prepared in phosphate buffered saline, without Ca$^{++}$ and Mg$^{++}$. The pieces immersed in this solution are kept at 4° C. for 16–18 hr. Using fine forceps, the epidermis is carefully separated from the dermis. Dermis is discarded (or used for growth of fibroblasts) and the epidermis is floated in a solution of ATV. When all epidermis is collected, the epidermal cells are separated from each other by mechanical teasing with forceps. The cells eluted into the supernatant are transferred into a new dish and further separated by vigorous pipetting with a pasteur pipette. The single cell suspension (checked under a microscope) is collected into fetal calf serum, removing any remaining clumps or pieces of tissue by filtration through 4 layers of sterile gauze mesh. To the remaining epidermal tissue, fresh ATV is added and the procedure as described above is repeated until all tissue is completely disaggregated. The cells collected in fetal calf serum are centrifuged at 1,000 rpm for 10 min., the supernatant discarded and the cells resuspended in GMEM, at pH 5.6–5.8 are counted. The viability of such cultures is usually approximately 90%. The cells are seeded at 5–8×10$^5$ cells/ml into plastic tissue culture vessels. GMEM is used for the growth of epidermal cells. The cells are grown in the presence of 5% CO$_2$ and 95% air, at 80% humidity and 35°–36° C.

What is claimed is:

1. Process for treating a burn victim which comprises:
   (i) separating the epidermis in a sample of human skin from the dermis;
   (ii) dissociating the epidermis into epidermal cells;
   (iii) growing the epidermal cells in the absence of dermal components into a pure epidermal sheet in a tissue culture medium having a pH of from about 5.6 to about 5.9; and
   (iv) applying the epidermal sheet to an afflicted area on the burn victim.

2. Process of claim 1 wherein clumps or pieces of tissue present after step (ii) are removed prior to step (iii).

3. Process of claim 1 wherein the culture medium contains from about 5 to about 15 percent by volume fetal calf serum.

4. Process of claim 3 wherein the culture medium contains about 10% by volume fetal calf serum.

5. Process of claim 4 wherein the epidermal cells are grown in a tissue culture vessel and the amount of fetal calf serum in the culture medium is reduced to about 5% by volume after the cells become attached to the vessel.

6. Process of claim 1 wherein the epidermal cells are seeded in the culture medium at a density of from about 5 to about 8×10$^5$ cells/ml.

7. Process of claim 1 wherein the cells are grown in the presence of atmospheric air.

8. Process of claim 7 wherein the air contains about 5% added carbon dioxide.

9. Process of claim 1 wherein the cells are grown at about 80% relative humidity.

10. Process of claim 1 wherein the cells are grown at a temperature of about 35°–36° C.

11. Process of claim 1 wherein the skin sample is from the burn victim.

12. Process of claim 11 wherein the epidermal sheet is applied by being first adhered to a transfer medium.

13. Process of claim 12 wherein the epidermal sheet is adhered to the dermal side of pig skin.

* * * * *

UNITED STATES PATENT AND TRADEMARK OFFICE
CERTIFICATE OF CORRECTION

PATENT NO. : 4,299,819
DATED : Nov. 10, 1981
INVENTOR(S) : Magdalena G. Eisinger It is certified that error appears in the above-identified patent and that said Letters Patent are hereby corrected as shown below:

Column 4, line 4   Delete "5.9" and insert --5.8--.

Signed and Sealed this

Twenty-seventh Day of April 1982

[SEAL]

Attest:

GERALD J. MOSSINGHOFF

Attesting Officer   Commissioner of Patents and Trademarks